United States Patent [19]

Badwal

[11] Patent Number: 4,720,993
[45] Date of Patent: Jan. 26, 1988

[54] SEMICONDUCTING OXYGEN SENSORS

[75] Inventor: Sukhyinder P. S. Badwal, Mulgrave, Australia

[73] Assignee: Commonwealth Scientific & Industrial Research Organization, Campbell, Australia

[21] Appl. No.: 882,883

[22] PCT Filed: Oct. 14, 1985

[86] PCT No.: PCT/AU85/00247
§ 371 Date: Jun. 16, 1986
§ 102(e) Date: Jun. 16, 1986

[87] PCT Pub. No.: WO86/02731
PCT Pub. Date: May 9, 1986

[30] Foreign Application Priority Data
Oct. 29, 1984 [AU] Australia ............... PG7876

[51] Int. Cl.$^4$ .................. G01N 27/12; G01N 27/14
[52] U.S. Cl. ...................... 73/23; 73/27 R; 324/71.5; 338/34
[58] Field of Search ............ 73/23, 27 R; 324/71.5; 340/634; 422/88, 94, 98; 338/34

[56] References Cited

U.S. PATENT DOCUMENTS

| | | | |
|---|---|---|---|
| 3,911,386 | 10/1975 | Beaudoin et al. | 338/34 |
| 4,178,793 | 12/1979 | Bremer et al. | 73/23 |
| 4,307,373 | 12/1981 | Johnston | 338/309 X |
| 4,358,950 | 11/1982 | Chang | 73/23 |
| 4,377,801 | 3/1983 | Weber et al. | 338/34 |

FOREIGN PATENT DOCUMENTS

| | | | |
|---|---|---|---|
| 203942 | 12/1982 | Japan | 73/23 |
| 3149 | 8/1984 | PCT Int'l Appl. | |
| 1427373 | 3/1976 | United Kingdom | 73/23 |
| 1460746 | 1/1977 | United Kingdom | |

OTHER PUBLICATIONS

"The Electrical Properties of Solid Oxide Electrolytes"; Chemical Reviews, 1970, vol. 70, No. 3, pp. 339-376; T. H. Etsell et al.

"Phase Equilibrium Studies in the $UO_2$-$ZrO_2$ System"; J. Inorg. Nucl. Chem.; 1967, vol. 29, pp. 1619-1630; K. A. Romberger et al.

"Ceramic Nuclear Fuels in the System $UO_2$-$ZrO_2$-CaO"; Journal of the American Ceramic Society; vol. 46, No. 1; pp. 29-32; Jan. 1963; J. H. Handwerk et al.

Handbook of Phase Diagrams of Silicate Systems; vol. II, "Metal-Oxygen Compound in Silicate Systems"; Translated from Russian by the Israel Program for Scientific Translations & published thereby for the U.S. Dept. of Commerce, National Bureau of Standards & The National Science Foundation, Washington, D.C.; N. A. Toropou et al., pp. 228-249; pub. by Jul. 1987.

J. Inorg. Nucl. Chem., 1967, vol. 29; pp. 45-50; in German, (English Abstract) "Elektronenbeugung Suntersuchung der Oxydation von $UO_2$ und der Struktur einer $U_3O_8$-oc-Üerstrukturphase"; S. Steeb et al.

"Urania-yttria Solid Solution Electrodes for High-Temperature Electrochemical Applications", Journal of Materials Science vol. 14, (1979); pp. 2353-2365; S. P. S. Badwal et al.

9P 278, Japatic English Language Abstract of Japanese Published Application No. 59-26041, 59-26041 Pub. Feb. 10, 1984, Japatic English Language Abstract Published by Jan. 1986.

(List continued on next page.)

Primary Examiner—Tom Noland
Attorney, Agent, or Firm—Kenyon & Kenyon

[57] ABSTRACT

A Sensor for measuring oxygen partial pressures in hot gases includes a semiconducting nonstoichiometric oxide material in the form of a solid solution in uranium dioxide $UO_2$ of at least one other metal oxide having an oxygen/metal (O/M) ratio of less than two and a uranium/other metal (U/M) ratio such that the material has n-type conductivity. The sensor further includes at least one pair of electrodes contacting the nonstoichiometric oxide material at spaced apart locations for connection to a device for determining the resistance of the material between the electrodes.

17 Claims, 8 Drawing Figures

OTHER PUBLICATIONS

"Solid-State Gas Sensors and Monitors"; *Electro-Chemistry, A Special Periodical Report*; vol. 9, pp. 246-285, 289; D. E. Williams et al.; The Royal Society of Chemistry; Published in 1984 by Burlington House, London.

"Phase Diagrams for Ceramists"; 1969 Supplement; pp. 51, 55, 138, & 139; Ernest McLevine et al., National Bureau of Standards, Published by The American Ceramic Society, Inc., in 1969.

*Handbook of Phase Diagrams of Silicate Systems*; vol. 1, "Binary Systems"; N. A. Toropov et al.; pp. 576-585, 706 & 707; Translated from Russian by the Israel Program of Scientific Translations & Pub. by National Bureau of Standards (U.S. Dept. of Commerce) and the National Science Foundation, Washington, D.C. by Oct. 1984.

"Measurements on Galvanic Cells Involving Solid Electrolytes; *Journal of The Electrochemical Society*"; Jun. 1957; vol. 104, No. 6, pp. 379-387; Kulevi Kiukkola et al.

SEMICONDUCTING OXYGEN SENSORS

BACKGROUND OF THE INVENTION

1. Technical Field

This invention concerns semiconducting nonstoichiometric oxide materials to be used as oxygen sensors to measure oxygen partial pressures in hot gases.

2. Description of the Related Art

Oxygen sensors based on the measurement of electrical resistivity of semiconducting oxides have been proposed. For example D. E. Williams and P. McGeehin in their article "Solid State Gas Sensors and Monitors" published in Electrochemistry, Vol 9, p 246-290 (1984) have discussed the characteristics of this and other types of sensors. Such devices are considered as alternatives to Nernst sensors which are currently used for measuring oxygen partial pressure in combustion products of boilers and car engines. An International patent application No. PCT/AU84/00013 describes one such Nernst sensor.

In the Nernst sensor, a solid electrolyte membrane wirh good oxygen ion conductivity and negligible electronic conductivity separates a reference gas from the test gas. When two electrodes reversible to the $O_2/O^{2-}$ redox equilibrium are placed in contact with the opposite faces of the membrane, an emf is established which is proportional to the oxygen concentration difference across the membrane. To avoid mixing of reference gas with the test gas, long impervious tubes of the solid electrolyte need to be used. Alternatively, hermetic seals are formed between a solid electrolyte membrane and a more robust tube of a ceramic or a metal.

On the other hand, the construction of a sensor based on measurement of electrical resistivity of a semiconducting nonstoichiometric oxide material is very simple and no hermetic seals are required. In its simplest form, the nonstoichiometric semiconducting oxide sensor consists of a porous disc of the material or a thin layer of the material painted on an insulator substrate such as alumina and two separate electrical contacts to measure the resistance. The principle of operation of a resistance measuring oxygen sensor is that the resistance of a semiconducting nonstoichiometric oxide material is represented by the expression:

$$R_o \propto \text{exponential } (E/RT) (pO_2)^n$$

where:
- $R_o$ = resistance of the material,
- T = the absolute temperature,
- E = the activation energy for conduction,
- $(pO_2)$ = the oxygen partial pressure, and
- R = the gas constant.

SUMMARY OF THE INVENTION

The value of n varies according to the defect chemistry of the nonstoichiometric oxide. The value of n for $TiO_2$, ZnO, $SnO_2$ or CoO based resistance sensors varies between 0.1 to 0.25. The sensitivity of the sensor to oxygen partial pressure changes increases and the relative error in oxygen partial pressure measure ment decreases with increasing values of n. If the value of E, the activation energy for conduction, is high then the sensor is subject to large errors due to fluctuations in the ambient temperature As an example, for an activation energy of 1eV, the temperature coefficient of resistance is 2.5%/°C. at 400° C. and 1.5%/°C. at 600° C. This, for a value of n of 0.200, will lead to about ±13% and ±7.5% errors respectively in oxygen partial pressure measurements for ±1° C. change in temperature. These errors are rather large in comparison with the Nernst sensor. Thus it is vital to measure the temperature of the sensing material accurately. Since this type of sensor can be of very small size, the accurate measurement, and control by an external heater, of temperature is relatively easy. Alternatively, from the known value of activation energy, correction for temperature deviation from the mean value will significantly reduce errors in oxygen partial pressure measurements.

Oxygen sensing devices based on measurement of resistance of semiconducting nonstoichiometric oxides in general have several advantages which may be summarized as:

(i) The construction of the sensor is extremely simple and the sensor can be prepared in any shape and size;

(ii) The sensors are very adaptable to miniaturization which enables accurate and uniform temperature control;

(iii) The current voltage relationship is linear and the sensitivity of the sensor can be increased by simply increasing the current;

(iv) Response time can be increased by construction of thin and/or porous films of the sensing material.

In principle, a large number of nonstoichiometric oxides can be used for measuring oxygen partial pressures. Limitations are imposed by:

Irreproducible value of n arising from material preparation, sensor geometry and other factors;

(ii) Slow oxidation kinetics at the gas/oxide interface;

(iii) Lack of linear relationship between resistance and oxygen partial pressure over the useful oxygen concentration range (0.1-10% $O_2$);

(iv) High value of activation energy or low value of n; and (v) Change in the surface conductivity due to adsorption of impurities from flue or other gases being measured.

Most of the known nonstoichiometric oxides suffer from one or more of these problems. The most successful ones have been those based on CoO, $TiO_2$ or $SnO_2$. However, even these need to be operated at temperatures of 600° C. or higher because of their slow oxidation/reduction kinetics.

One objective of the present invention is to provide an oxygen sensor comprising a semiconducting nonstoichiometric oxide material which does not suffer from one or more of the above-mentioned limitations. A further objective is to provide oxygen sensing devices comprising a semiconducting nonstoichiometric oxide material and which can be operated at temperatures down to 450° C. or below.

These oxide materials for use in accordance with the present invention are solid solutions in uranium dioxide of one or more other metal oxides having an oxygen/metal (O/M) atom ratio of less than two. These solid solutions have a face-centered cubic crystal structure similar to that of calcium fluoride (fluorite), hereinafter referred to as the fluorite structure. In these solid solutions, the average oxidation state of the uranium (U) increases with decrease in the U/M atom ratio. For U/M atom ratios less than a certain value, the solid solutions become n-type conductors. For example when M = such metals as Y, Gd, Dy, Pr, La, or Nd, this U/M atom ratio is around 0.34/0.66. As the U/M atom ratio decreases below about 0.25/0.75, the fluorite-type phase coexists with one or more other phases. It is accordingly this narrow solid solution range between U/M atom ratios of 0.34/0.66 and 0.25/0.75 which is of particular interest as regards the present invention. The fluorite-type lattice is anion deficient and the O/(U+M) atom ratio is less than two.

Solid solutions of the general formula $(U,M)O_{2\pm x}$ (where the subscript "$2\pm x$" indicates a small departure from an O/(U+M) atom ratio of 2) and having the fluorite structure are listed in the compilation "Phase Diagrams for Ceramists" published by the American Ceramic Society and in "Handbook of Phase Diagrams of Silicate Systems" Vol. I, "Binary Systems" by N. A. Toropov, V. P Barzakovskii, V. V. Lapin and N. N. Kurtseva published by the U.S. Department of Commerce, National Bureau of Standards. The fluorite-type solid solutions of the present invention for which uranium reaches its highest oxidation state (U/M ratio between 0.34/0.66 and 0.25/0.75) have never been used or suggested for oxygen sensing applications at high (>600° C.) or low (<600° C.) temperatures. S. P. S. Badwal and D. J. M. Bevan, in their article "Urania Yttria solid solution electrodes for high temperature electrochemical applications" published in the Journal of Materials Science, volume 14, 1979 at page 2353 have merely reported the electrical conductivity of one such composition i.e. $(U_{0.3}Y_{0.7})O_{2-x}$.

The nonstoichiometric oxide materials of the present invention have high electrical resistivity at room temperature. At higher temperatures, the O/(U+M) atom ratio varies with the oxygen partial pressure. As the oxygen partial pressure decreases, the oxygen from the lattice positions is lost leaving electrons behind. As a result of this process the electrical resistivity at a constant temperature decreases with decrease in the oxygen partial pressure.

Accordingly the present invention provides a sensor for the measurement of oxygen partial pressures in hot gases comprising a semiconducting nonstoichiometric oxide sensing material and a pair of mutually spaced electrodes in contact with said material, the said material being in the form of a solid solution in uranium dioxide of one or more other metal oxides having an oxygen/metal (O/M) atom ratio of less than two, and the uranium/other metal (U/M) atom ratio being such that the said material has n-type conductivity. Usually the uranium/other metal (U/M) atom ratio is within the range of 0.34/0.66 to 0.25/0.75.

According to one embodiment of the invention, the nonstoichiometric oxide sensing material may be present in the sensor in admixture with at least one noble metal selected from the group consisting of platinum, gold, silver, palladium and alloys of any two or more of these elements.

The sensing material may be in the form of a porous disc or block, or it may be applied as a paste or other layer on an insulator substrate. The substrate may have high or low porosity and may be fully or partially sintererd.

According to a further aspect of the invention, the sensor may incorporate one or more insulator, ionic conductor or other semiconductor phases. For example, the sensing material may be applied in the form of a mixture with a glass to a substrate such as alumina, or it may be bonded to a substrate by means of an intermediate layer of glass or other suitable material.

It is also within the scope of this invention that the sensing material contains a proportion of free uranium oxide or the other oxide component or components of the $(U,M)O_{2\pm x}$ solid solution or ordered phases in the uranium oxide-metal oxide-oxygen system.

In a preferred form of the invention the sensing material contains dopant oxide of the general formula $M_2O_3$ such as $Y_2O_3$, $Gd_2O_3$ or $La_2O_3$, the U/M atom ratio falling within the range 0.34/0.66 to 0.25/0.75.

The invention also includes methods for preparing the oxygen sensing devices. For fast response, the sensing material may comprise a thin porous coating on a substrate in the form of an insulator or it may be prepared by suitable known coating methods such as screen-printing, painting, spraying, sputtering, ion implantation or other in-situ chemical techniques.

Where external heating is required in order to heat the gas and/or provide accurate temperature control, a heating element and metal connections to the sensing material may also be applied to the substrate by techniques such as screen-printing or sputtering.

The invention further includes a method of measuring oxygen partial pressure $pO_2$ in a hot gas at a certain temperature which comprises the steps of:
(a) determining the calibration constant $R_1$, being the resistance at the said certain temperature of a sensor according to the invention in an atmosphere having a known oxygen partial pressure $p^cO_2$;
(b) determining the resistance $R_O$ at the said certain temperature of the sensor in the hot gas whose oxygen partial pressure $p^uO_2$ is to be measured; and
(c) using the formula $$p^uO_2 \text{ (atm)} = p^cO_2 (R_0/R_1)^{1/n}$$

to calculate the oxygen partial pressure in the hot gas, where n has a predetermined value for the sensing material of the sensor at the said certain temperature and is a measure of the defect chemistry of the sensing material.

The invention also includes a method of measuring oxygen partial pressure $p^uO_2$ in a hot gas which comprises the steps of:
(a) determining the calibration constant $R_1$ being the resistance at a known temperature of a sensor according to the invention in an atmosphere having a known oxygen partial pressure $p^cO_2$;
(b) determining the resistance $R_0$ of the sensor in the hot gas whose oxygen partial pressure $p^uO_2$ is to be measured;
(c) determining the temperature T of the hot gas at which the resistance $R_0$ is determined and applying a correction to the calibration constant $R_1$ for variation of temperature T from said known temperature making use of the known relationship $$R_1 \propto \text{exponential } (E/RT)$$

where
E = the activation energy for conduction,
R = the gas constant, and
T is in degrees absolute;
(d) determining the modified value (n') of n at the temperature of the sensor from a previously known relationship between n and temperature; and
(e) using the formula $$p^uO_2 \text{ (atm)} = p^cO_2 (R_0/R_1')^{1/n'}$$

to calculate the oxygen partial pressure in the hot gas, where $R_1^c$ is the corrected calibration constant.

BRIEF DESCRIPTION OF THE DRAWINGS

In the following description reference will be made to the accompanying drawings, in which.

DESCRIPTION OF THE PREFERRED EMBODIMENTS

Figure 1:
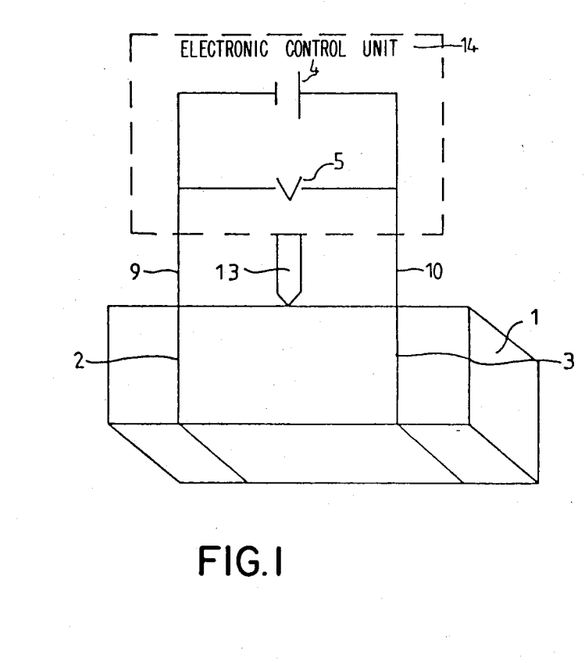
FIGS. 1 to 6 show various forms of oxygen sensors according to the invention.
Figure 2:
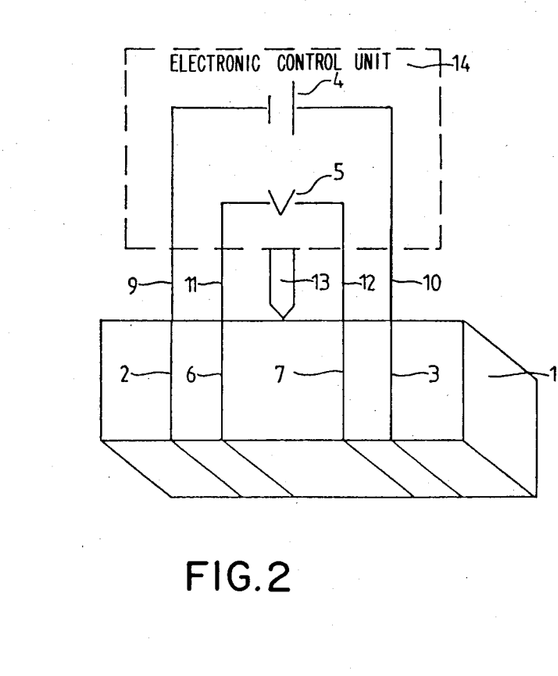
Figure 3:
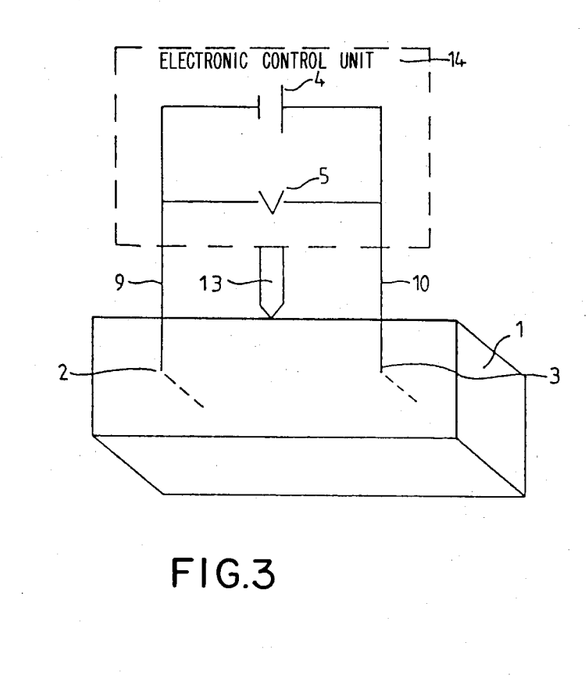
Figure 4:
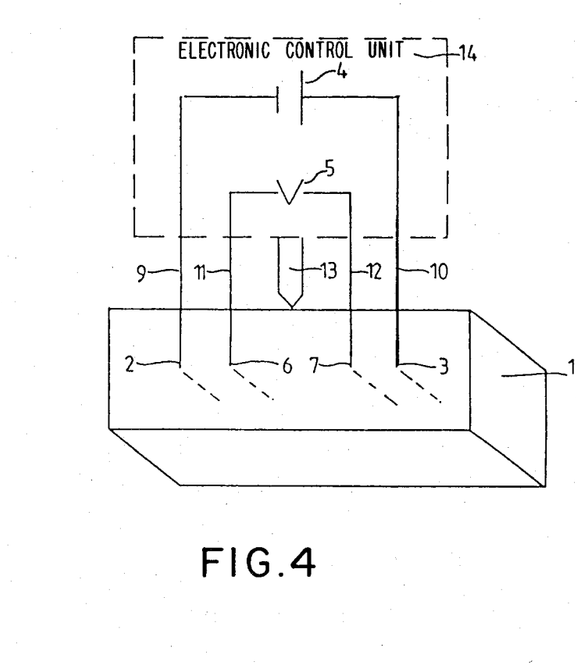
Figure 5:
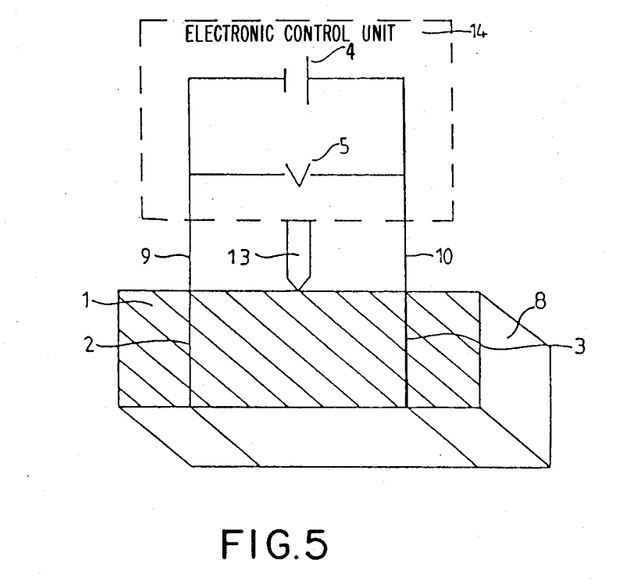
Figure 6:
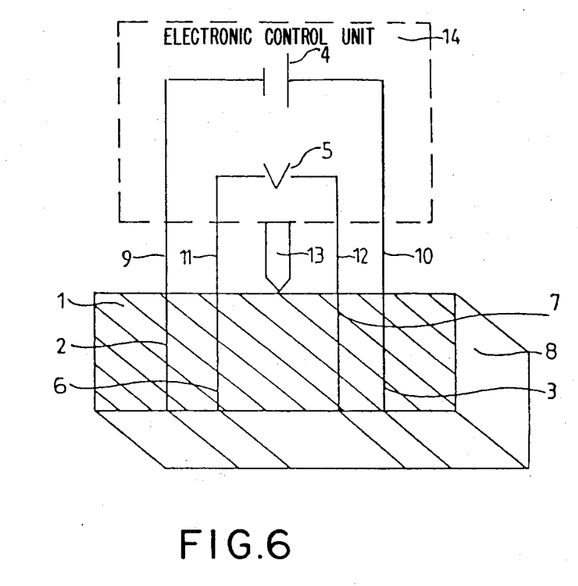

Three forms of sensor incorporating sensing materials of the present invention are shown in FIGS. 1 to 6. FIGS. 1, 3, and 5 represent a two probe assembly including electrical contacts 2 and 3, while FIGS. 2, 4 and 6 represent a four probe assembly including electrical contacts 2, 3, 6 and 7. For most applications a two probe assembly is adequate. The advantage of the four probe assembly is that the contact resistance at electrodes 2 and 3 is eliminated. In environments where contact resistance is likely to change due to thermal or mechanical shocks or due to reaction between the contact material and hot gases, it is preferable to use a four probe assembly. In FIGS. 1, 2, 3 and 4, the sensor material 1 of the present invention is in the form of a porous block or disc whereas in FIGS. 5 and 6, it is in the form of a thin porous coating 1 on a substrate 8 of an insulator material such as alumina.

The electrical contacts can be constructed by simply wrapping a wire of any suitable metal or alloy around the sensor material (FIGS. 1, 2, 5 and 6). Alternatively the contacts can be embedded in the sensor material (FIGS. 3 and 4) during or after fabrication of the block, disc or thin coating. Another alternative to the above for making electrical contacts to the sensor material is to use coatings of metals such as platinum, silver, gold, or palladium and/or their alloys or a mixture of the sensor material with noble metals and/or their alloys. These coatings may be in the form of a point contact or continuous strips.

For measuring resistance, electrical contacts 2 and 3, (for the two probe arrangement) and 2, 3, 6 and 7 (for the four probe arrangement) are connected to an electronic control unit 14 via wires 9 and 10, or 9, 10, 11 and 12 respectively. These wires may be made of any suitable metal or alloy. In order to avoid thermocouple effects, it is desirable that all wires 9, 10, 11 and 12 be of the same metal or alloy. A thermocouple 13 makes direct contact with the sensor material 1 for accurate measurement of temperature.

The two probe assembly may be further simplified by using one leg of the thermocouple as one of the connections to the resistance sensing device. Under such circumstances it is desirable that the second connecting wire (to the resistance sensing device) be of the same material as the said one leg of the thermocouple to avoid thermocouple effects.

The electronic control unit 14 measures the resistance and temperature of the sensor. In its simplest form, it consists of a resistance meter and a temperature measuring device. The resistance meter may be replaced by a constant current source 4 to pass current and a voltmeter 5 to measure the voltage signal. Alternatively, the resistance meter may be replaced by a constant voltage source and a current measuring device. In addition, the electronic control unit may perform complex functions such as calibration of the sensor and accurate control and measurement of temperature of the sensor when an external heater is provided to heat the sensor. A microprocessor based electronic control unit may also store variables such as the values of the activation energy and n for automatic compensation for temperature deviations from the calibration temperature of the sensor and calculations of the oxygen partial pressure as discussed more fully hereinafter.

The following examples illustrate the preparation and electrical properties of the sensing material of the present invention and behavior of the oxygen sensor in the laboratory.

EXAMPLE 1

A powder of composition $(U_{0.3}Y_{0.7})O_{2-x}$ was prepared by coprecipitation of the hydroxide with aqueous ammonia from a solution containing the required proportions of uranyl and yttrium nitrates followed by drying and calcination in air at 700° C. Room temperature x-ray diffraction confirmed the presence of a single fluorite phase.

EXAMPLE 2

The $(U_{0.3}Y_{0.7})O_{2-x}$ powder prepared according to example 1 was pressed into a disc form and sintered at 1300° C. in air. Platinum was then sputtered on two flat faces of the disc (cell A). The resistance of this disc was determined at 600° C. and 500° C. using two probe AC technique at varying frequencies in various oxygen partial pressures. The relationship between Log $R_o$ and Log $pO_2$ was found to be linear and the value of n determined from Log $R_o$ versus Log $pO_2$ plots by linear least squares analyses is given in Table 1.

TABLE 1

Values of n over oxygen partial pressure range 1.0 to 0.003 atm for $(U_{0.3}Y_{0.7})O_{2-x}$.

| | n Temperature, °C. | | | | |
|---|---|---|---|---|---|
| Sensor | 400 | 500 | 600 | 700 | 800 |
| Example 2 - cell A | — | 0.218 | 0.198 | — | — |
| Example 3 - cell B | 0.227 | 0.217 | 0.199 | 0.177 | 0.147 |
| Example 4 - cell C | 0.227 | 0.220 | 0.201 | — | — |
| Example 5 - cell D | 0.238 | — | 0.200 | — | — |

EXAMPLE 3

Figure 7:
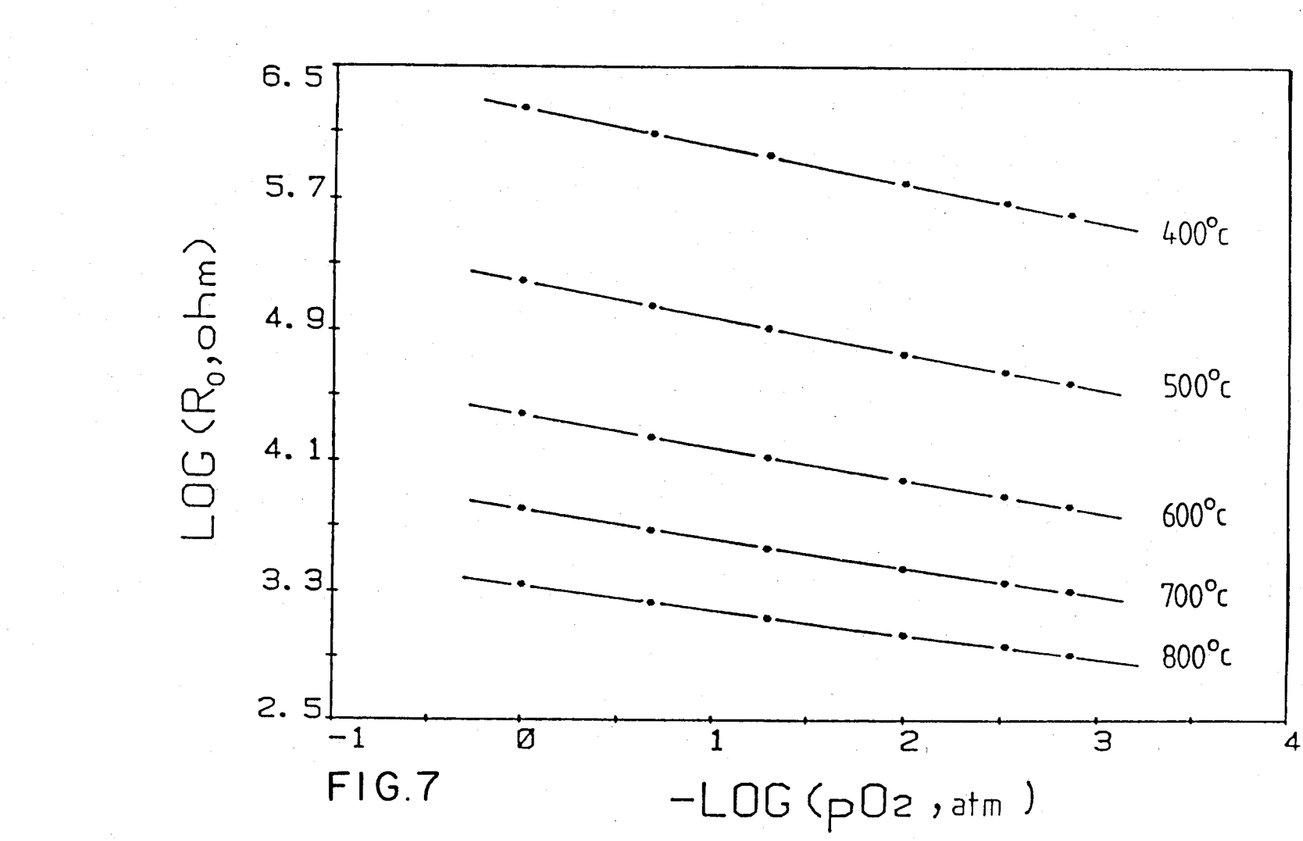
FIG. 7 is a graph showing the variation in the electrical resistance of a sensing material of the invention with oxygen partial pressure, at different temperatures.
Figure 8:
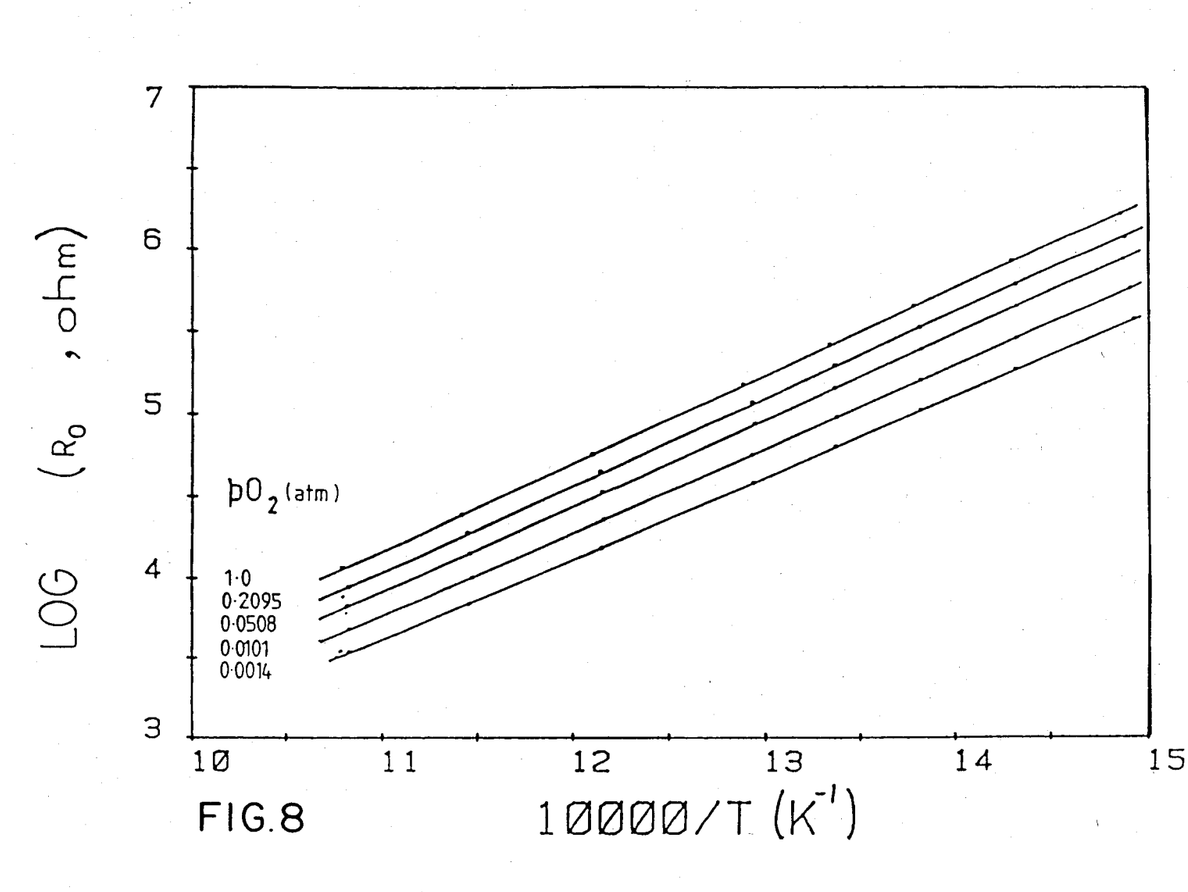
FIG. 8 is a graph in the form of Arrhenius plots showing the variation in the electrical resistance of a sensing material of the invention with temperature for different oxygen partial pressures.

The $(U_{0.3}Y_{0.7})O_{2-x}$ powder prepared according to example 1 was pressed into a disc form and sintered at 1300° C. in air. The electrical contacts were made by wrapping two platinum wires around the disc (cell B). Measurements of resistance as a function of oxygen partial pressure were made at 400°, 500°, 600°, 700° and 800° C. and the results are shown in FIG. 7. Between 1.0-0.003 atm of oxygen partial pressure, the relationship between Log $R_o$ and Log $pO_2$ was linear. The value of n at various temperatures is given in Table 1. The activation energy for conduction determined over the temperature range 400°–650° C. in various oxygen partial pressures is given in Table 2. FIG. 8 shows plots of the electrical resistance versus reciprocal temperature in various oxygen partial pressures.

TABLE 2

Activation energy (kCal/mol) for conduction in various oxygen partial pressures for $(U_{0.3}Y_{0.7})O_{2-x}$

| Sensor | E, kCal/mol Oxygen partial pressure (atm) | | | | |
|---|---|---|---|---|---|
|  | 1.0 | 0.2095 | 0.0508 | 0.0101 | 0.0014 |
| cell B | 24.32 ± 0.2 | 23.85 ± 0.25 | 23.66 ± 0.10 | 23.34 ± 0.2 | 22.75 ± 0.15 |
| cell C | 24.20 ± 0.2 | — | — | — | — |
| cell D | 24.46 ± 0.2 | — | — | — | — |

EXAMPLE 4

The $(U_{0.3}Y_{0.7})O_{2-x}$ powder prepared according to example 1 was pressed into a disc shape and sintered at 1400° C. in air. Four electrical contacts to the disc were made by wrapping platinum wire around the disc as in FIG. 2. Two outer contacts 2 and 3 were used for passing constant current through the sensing material and two inner contacts 6 and 7 were used for measuring the voltage signal (cell C). In addition, two probe measurements were made on this sample according to the configuration in FIG. 1 using wire contacts 2 and 3. Measurements of resistance, by both the four probe and the two probe techniques, in various oxygen partial pressures were made at 600°, 500° and 400° C. Table 1 gives values of n determined from Log $R_o$ versus Log $pO_2$ plots.

EXAMPLE 5

The $(U_{0.3}Y_{0.7})O_{2-x}$ powder prepared according to example 1 was painted on an alumina disc (FIG. 5) as a fine paste in tri-ethylene glycol and the disc heated at 600° C. in air. Two contacts to the sensing material were made by wrapping platinum wire around the alumina disc (cell D). Resistance measurements in various oxygen partial pressures were made at 600° and 400° C. and values of n are given in Table 1.

EXAMPLE 6

The $(U_{0.3}Y_{0.7})O_{2-x}$ powder prepared according to example 1 was pressed into a disc form and sintered at 1300° C. in air. Two electrical contacts were made by wrapping platinum wires around the disc The resistance was monitored continuously while the gas atmosphere around the sensing material was changed back and forth between 5% oxygen in nitrogen, 10% hydrogen in nitrogen, and a mixture containing oxygen, nitrogen, acetone and water vapour. The resistance was found to be orders of magnitude lower in reducing atmospheres.

These examples demonstrate that the value of n at a constant temperature is independent of the method of preparation of the sensing material, sensor geometry, and the techniques used to measure the resistance. Also the relationship between Log $R_o$ and Log $pO_2$ is linear at least over an oxygen partial pressure range of 1.0 to 0.003 atm. Thus at a constant temperature, an unknown oxygen partial pressure is given by:

$$p^uO_2(atm) = (R_0/R_1)^{1/n}$$

where $R_1$ is a calibration constant and is the resistance of the sensor in an oxygen partial pressure of one atmosphere and $R_o$ is the resistance of the sensor in an atmosphere whose oxygen partial pressure, $p^uO_2$, is to be measured.

If air is used to calibrate the sensor then $$p^uO_2 (atm) = 0.2095 (R_0/R_1)^{1/n}$$

and now $R_1$ is the resistance of the sensor in air.

In circumstances where use of an external heater to accurately control the temperature of the sensor is undesirable, and in enviroments where temperature fluctuations occur, correction for temperature variation can be applied from the known relationship between activation energy and oxygen partial pressure, and n and temperature.

EXAMPLE 7

The $(U_{0.3}Y_{0.7})O_{2-x}$ powder prepared according to example 1 was pressed into a bar shape and sintered at 1300° C. in air. Two electrical contacts were made by painting platinum paste on to the ends of the bar, heating at 800° C. in air for 15 hours and wrapping platinum wires over the platinum paste. The sensor thus produced was placed in a furnace and heated to a constant temperature (600° C.±1° C.). A thermocouple to monitor the temperature of the sensor and electrical lead wires to measure the resistance of the sensor were connected to a microprocessor based equipment.

At the start of the experiment, the resistance of the sensor ($R_1$) was measured in air ($pO_2 = 0.2095$ atm) and the result of the measurement stored in the microprocessor as the value for the calibration constant. In addition the values of n at various temperatures were also stored in the microprocessor for use in calculation of the oxygen partial pressure later on.

In the first stage of the experiment the temperature of the sensor was kept constant to within ±1° C. and the oxygen partial pressure around the sensor was changed regularly. The resistance of the sensor was monitored continuously, over a period of 3-4 weeks and oxygen partial pressure determined using the relationship:

$$pO_2 (atm) = 0.2095 (R_0/R_1)^{1/n}$$

where $R_O$ is the resistance of the sensor determined in various oxygen partial pressures after the initial calibration. Over this period, without recalibration, the errors in oxygen partial pressure measurements increased only to less than 5 percent.

In the second stage of the experiment, the sensor was continuously cycled firstly between 600° C. and 300° C. at heating and cooling rates of 0.5° C. $\min^{-1}$ for 25 days and then between 600° C. and 20° C. at heating and cooling rates of 1.0° C. $\min^{-1}$ for 19 days. The resistance and temperature of the sensor were monitored continuously with the microprocessor based equipment.

The procedure for calculating oxygen partial pressure at a temperature different from the calibration temperature of 600° C. involved:

(i) accurately determining the temperature and resistance of the sensor;

(ii) calculating the new value for the calibration constant ($R_1$) at the temperature of the sensor from the known relationship:

$$R_1 \propto \text{exponential } (E/RT)$$

where E is the activation energy for conduction in air (Table 2), R is the gas constant and T is the temperature of the sensor in degrees absolute at the time of measuring the resistance; and (iii) calculating the oxygen partial pressure using the relationship:

$$pO_2 (atm) = 0.2095 (R_0/R_1)^{1/n'}$$

where $n'$ is the modified value of n at the temperature of the sensor calculated by the microprocessor from a polynomial fit to the data in Table 1.

The sensor measured accurate oxygen partial pressures ($\pm 10$ percent) down to a temperature of 380° C. during cooling below which the errors increased significantly. However, during heating, either from 300° C. or 20° C., the sensor started measuring accurate oxygen partial pressures around 390°–400° C.

These results demonstrate that sensors of the present invention can be used to monitor oxygen partial pressure in hot gases at least between 1 atm and 0.003 atm. Many applications (for example, boilers or lean operation of car engines) require the oxygen partial pressure to be monitored only between 0.1 and 0.01 atm and the present invention can be used well beyond this range. The results of example 6 indicate that sensors of the present invention may also be used to monitor the stoichiometric air/fuel ratio.

Those skilled in the art will appreciate that the invention described herein is susceptible to variations and modifications other than those specifically described. It is therefore to be understood that the invention includes all such variations and modifications which fall within its spirit and scope.

I claim:

1. A sensor for the measurement of oxygen partial pressures in hot gases comprising a semiconducting nonstroichiometric oxide sensing material and a pair of mutually spaced electrodes in contact with said material, the said material being in the form of a solid solution in uranium dioxide of at least one other metal oxide having an oxygen/metal (O/M) atom ratio of less than two, and the uranium/other metal (U/M) atom ratio being such that the said material has n-type conductivity.

2. A sensor according to claim 1, wherein the uranium/other metal (U/M) atom ratio is within the range of 0.34/0.66 to 0.25/0.75.

3. A sensor according to claim 1 or claim 2, further comprising an additional pair of mutually spaced electrodes in contact with said semiconducting nonstoichiometric oxide sensing material.

4. A sensor according to claim 1 or claim 2, wherein the said other metal oxide has an oxygen/metal (O/M) atom ratio of 3/2.

5. A sensor according to claim 1 or claim 2, wherein the said other metal is Y, Gd, Dy, Pr, La, or Nd.

6. A sensor according to claim 1 or claim 2, wherein the semiconducting nonstoichometric oxide sensing material is mixed with at least one noble metal selected from the group consisting of platinum, gold, silver, palladium and alloys of at least two of these metals.

7. A sensor according to claim 1 or claim 2, wherein the semiconducting nonstoichiometric oxide sensing material contains a proportion of free material selected from the group consisting of uranium dioxide, at least one other oxide component of the solid solution, and ordered phases in the uranium oxide-metal oxide-oxygen system.

8. A sensor according to claim 1 or 2, further comprising at least one phase selected form the group consisting of insulator, ionic conductor, and other semiconductor phases.

9. A senosor according to claim 1 or claim 2, wherein the semiconducting nonstoichometric oxide sensing material is applied as a layer on an insulator substrate.

10. A sensor according to claim 1 or claim 2, wherein the semiconducting nonstoichiometric oxide sensing material is applied as a layer on an at least partly sintered insulator substrate.

11. A sensor according to claim 1 or claim 2, wherein the semiconducting nonstoichiometric oxide sensing material is applied in a mixture with glass to a substrate.

12. A sensor according to claim 1 or claim 2, wherein the semiconducting nonstoichiometric oxide sensing material is bonded to a substrate by measn of an intermediate layer.

13. A sensor according to claim 1 or claim 2, wherein the semiconducting nonstoichiometric oxide sensing material is in the form of a porous disc or block.

14. A sensor according to claim 1 or claim 2, further comprising a resistance measuring device.

15. A sensor according to claim 1 or claim 2, further comprising a resistance measuring device which comprises a constant current source to pass current and a voltmeter to measure the voltage signal.

16. A sensor according to claim 1 or claim 2, further comprising a temperature measuring device for measuring the temperature of the sensor.

17. A sensor according to claim 1 or claim 2, further comprising a thermocouple for measuring the temperature of the sensor.

* * * * *

UNITED STATES PATENT AND TRADEMARK OFFICE
CERTIFICATE OF CORRECTION

PATENT NO. : 4,720,993

DATED : 26 January 1988

INVENTOR(S) : Sukhvinder P.S. BADWAL

It is certified that error appears in the above-identified patent and that said Letters Patent is hereby corrected as shown below:

Front Title Page, Column 2, line 13: Change "Toropou" to --Toropov--.

Front Title Page, Column 2, lines 15-16: Change "Elektronenbeugung Suntersuchung" to --Elektronenbeugungsuntersuchung--.

Front Title Page, Column 2, line 17: Change "Üerstrukturphase" to --Überstrukturphase--.

Front Title Page, Column 2, line 23: Change "Pub." to --pub.--.

Front Title Page, Column 2, line 24: Change "Pub." to --pub.--.

Front Page 2, Column 2, line 3: Change "Pub." to --pub.--.

Column 1, line 61: Change "measure ment" to --measurement--.

Column 6, line 55: Change "EXAMPLE3" to --EXAMPLE 3--.

Column 10, line 22: Change "senosor" to --sensor--.

UNITED STATES PATENT AND TRADEMARK OFFICE
CERTIFICATE OF CORRECTION

PATENT NO. : 4,720,993

DATED : January 26, 1988

INVENTOR(S) : Sukhvinder P.S. Badwal

It is certified that error appears in the above-identified patent and that said Letters Patent is hereby corrected as shown below:

Column 10, line 35: Change "measn" to --means--.

Signed and Sealed this

Nineteenth Day of July, 1988

Attest:

DONALD J. QUIGG

Attesting Officer

Commissioner of Patents and Trademarks